(12) United States Patent
Tsuchida et al.

(10) Patent No.: US 6,391,576 B1
(45) Date of Patent: May 21, 2002

(54) METHOD FOR ISOLATING A MICROBE

(75) Inventors: Takayasu Tsuchida, Yokohama; Akira Manome, Tsukuba; Ryuichiro Kurane, Matsudo, all of (JP)

(73) Assignees: Japan Bioindustry Association; Ajinomoto Co., Inc.; Agency of Industrial Science and Technology, all of Tokyo (JP)

( * ) Notice: Subject to any disclaimer, the term of this patent is extended or adjusted under 35 U.S.C. 154(b) by 0 days.

(21) Appl. No.: 09/517,744

(22) Filed: Mar. 3, 2000

(30) Foreign Application Priority Data

Oct. 13, 1999 (JP) ............................. 11-291297
Nov. 19, 1999 (JP) ............................. 11-330419

(51) Int. Cl.$^7$ ................................. C12Q 1/24
(52) U.S. Cl. ........................... 435/30; 435/182
(58) Field of Search .................. 435/30, 179, 182, 435/382

(56) References Cited

U.S. PATENT DOCUMENTS 4,647,536 A * 3/1987 Mosbach et al. ............ 435/177
4,659,655 A * 4/1987 Rose ............................. 435/7
4,695,548 A * 9/1987 Cantor et al. ............... 435/179
4,927,761 A * 5/1990 Reading et al. ............. 435/178
5,643,569 A * 7/1997 Jain et al. ................... 424/93.7

FOREIGN PATENT DOCUMENTS

JP          07252157        * 10/1995

* cited by examiner

*Primary Examiner*—Ralph Gitomer
(74) *Attorney, Agent, or Firm*—Oblon, Spivak, McClelland, Maier & Neustadt, P.C.

(57) ABSTRACT

The present invention provides a method for isolating a microbe whereby a sample of microbe cells is encapsulated in agarose gel particulates, wherein some of the particulates contain a single cell, and the other particulates contain more than one cell; incubating the particulates in nutritional and environmental conditions that enable the microbe contained in the sample solution that can grow on a plate of a plate culture method to grow in the agarose gel particulate; and isolating the particulates having single cells from the group of the particulates having more than one cell.

12 Claims, 5 Drawing Sheets

SEQUENCE LISTING

```
<160> NUMBER OF SEQ ID NOS: 1

<210> SEQ ID NO 1
<211> LENGTH: 1407
<212> TYPE: DNA
<213> ORGANISM: Paracoccus kawasakiensis

<400> SEQUENCE: 1
taaagttgat catggctcag aacgaacgct ggcggcaggc ctaacacatg c aagtcgagc      60 gcgcccttcg gggtgagcgg cggacgggtg agtaacgcgt gggaacgtgc c cttctctac     120 ggaatagtct cgggaaactg ggggtaatac cgtatacgct cttcggagga a agatttatc    180 ggagaaggat cggcccgcgt tggattaggt agttggtgag gtaacggctc a ccaagccga    240 cgatccatag ctggtttgag aggatgatca gccacactgg gactgagaca c ggcccagac    300 tcctacggga ggcagcagtg gggaatctta gacaatgggg gaaaccctga t ctagccatg    360 ccgcgtgagc gatgaaggcc ttagggttgt aaagctcttt cagctgggaa g ataatgacg    420 gtaccagcag aagaagcccc ggctaactcc gtgccagcag ccgcggtaat a cggaggggg    480 ctagcgttgt tcggaattac tgggcgtaaa gcgcacgtag gcggatcaga a agtcagagg    540 tgaaatccca gggctcaacc ttggaactgc ctttgaaact cctggtcttg a ggtcgagag    600 aggtgagtgg aattccgagt gtagaggtga aattcgtaga tattcggagg a acaccagtg    660 gcgaaggcgg ctcactggct cgatactgac gctgaggtgc gaaagcgtgg g gagcaaaca    720 ggattagata ccctggtagt ccacgccgta aacgatgaat gccagacgtc g ggcagcatg    780 ctgttcggtg tcacacctaa cggattaagc attccgcctg gggagtacgg c cgcaaggtt    840 aaaactcaaa ggaattgacg ggggcccgca caagcggtgg agcatgtggt t taattcgaa    900 gcaacgcgca gaaccttacc aacccttgac atggagggga ccgttccaga g atggttctt    960 tctcgtaaga gacccctcgc acaggtgctg catggctgtc gtcagctcgt g tcgtgagat    1020 gttcggttaa gtccggcaac gagcgcaacc cacactcctg gttgccagca t tcagttggg    1080
```

-continued

```
cactttagga gaactgccgg tgataagccg gaggaaggtg tggatgacgt c aagtcctca   1140 tggcccttac gggttgggct acacacgtgc tacaatggtg gtgacaatgg g ccaatccca   1200 aaaagccatc tcagttcgga ttgggtctg caactcgacc ccatgaagtc g gaatcgcta    1260 gtaatcgcgt aacagcatga cgcggtgaat acgttcccgg gccttgtaca c accgcccgt   1320 cacaccatgg gaattgggtc tacccgacga cggtgcgcta acccgcaagg g aggcagccg   1380 gccacggtag gctcagtgac tggggtg                                        1407
```

METHOD FOR ISOLATING A MICROBE

BACKGROUND OF THE INVENTION

1. Field of the Invention

The present invention relates to a method for isolating a microorganism, and more particularly to a method for isolating a microbe which would otherwise be difficult to isolate using conventional plate culture methods.

2. Discussion of the Background

Conventionally, isolation of a microbe has been conducted by a plate culture method. This method includes spreading a sample solution containing various species of microbes and placing the seeded plates in nutritional and environmental conditions which enable the microbes to grow and form colonies on the plates. Subsequently, the formed colonies are isolated from the plate. However, the plate culture method is not useful for isolating a microbe that is unable to form colonies on the plate under the conventional nutritional and environmental conditions of the plate culture method. To find suitable conditions, plating is usually repeated many times under various nutritional and environmental conditions until such time that the microbe will form a colony. However, it is an impractability to formulate and prepare suitable nutritional and environmental conditions which allow unknown microbe species to grow on a plate for subsequent isolation.

In view of the above, only limited microbe species can be isolated from a sample containing various microbe species by the plate culture method. For example, Torsvik et al (Appl. Environ. Microbiol. 56, 782–787 (1990)) report that the proportion of microorganisms capable of forming a colony was 0.3% of all microorganisms existing in soil. Wagner et al (Appl. Environ. Microbiol. 59, 1520–1525 (1993)) report that the proportion of microorganisms capable of forming a colony was only 1 to 15% of all bacteria existing in active sludge. Staley et al (Annu. Rev. Microbiol. 39, 66–68 (1985)) report that the proportion of microorganisms capable of forming a colony was 0.1 to 1% of all microorganisms existing in neutral lake water. Ferguson et al (Appl. Environ. Microbiol. 42, 49–55 (1984)) and Kogure et al (Can. J. Microbiol. 25, 415–420 (1979) and Can. J. Microbiol. 26, 318–323 (1980) examined microbes in the sea and report that the proportion of microbes capable of forming a colony was 0.001 to 0.1% of all microorganisms in the sea. Jones (Freshwater Biol. 7, 67–91 (1997)) examined lake water and sediments and reports that the proportion of microbes capable of forming a colony was 0.25% of all microbes in both cases.

Although a considerably large number of microbe species fail to be isolated by the plate culture method as described above, isolation of such microbe species is intensely required in various fields. Examples of such fields includes the food industry, the medical and pharmaceutical industries, and environmental protection from pollution such as water protection. Furthermore, it is necessary to isolate microbe species of which isolation is difficult by the plate culture method for finding and utilizing novel functions of such microbes or for suppressing harmful activities thereof in the natural environment. Examples of such microbes are those that may be found in extreme environments such as the deep sea and from organisms such as humans, insects, soil protozoa, and sea organisms. Thus, a significant need exists for the isolation of microbe species that could not normally be isolated by prior methods of microbe isolation, e.g., plate culture methods.

SUMMARY OF THE INVENTION

Thus, the object of the present invention is to provide a method for isolating a microbe species from a sample containing various microbe species whereby isolation by the known plate culture method would otherwise be difficult.

This object is achieved by the present method comprising the steps of:

encapsulating microbe cells in agarose gel particulates, wherein some of the particulates contain a single cell, whereas the other particulates contain more than one cell;

subsequently incubating the particulates in nutritional and environmental conditions that enable the microbe contained in the sample solution that can grow on a plate of a plate culture method to grow in the agarose gel particulate; and after incubation, isolating the particulates having single cells from the group of the particulates having more than one cell.

DETAILED DESCRIPTION OF THE PREFERRED EMBODIMENTS

Figure 1:
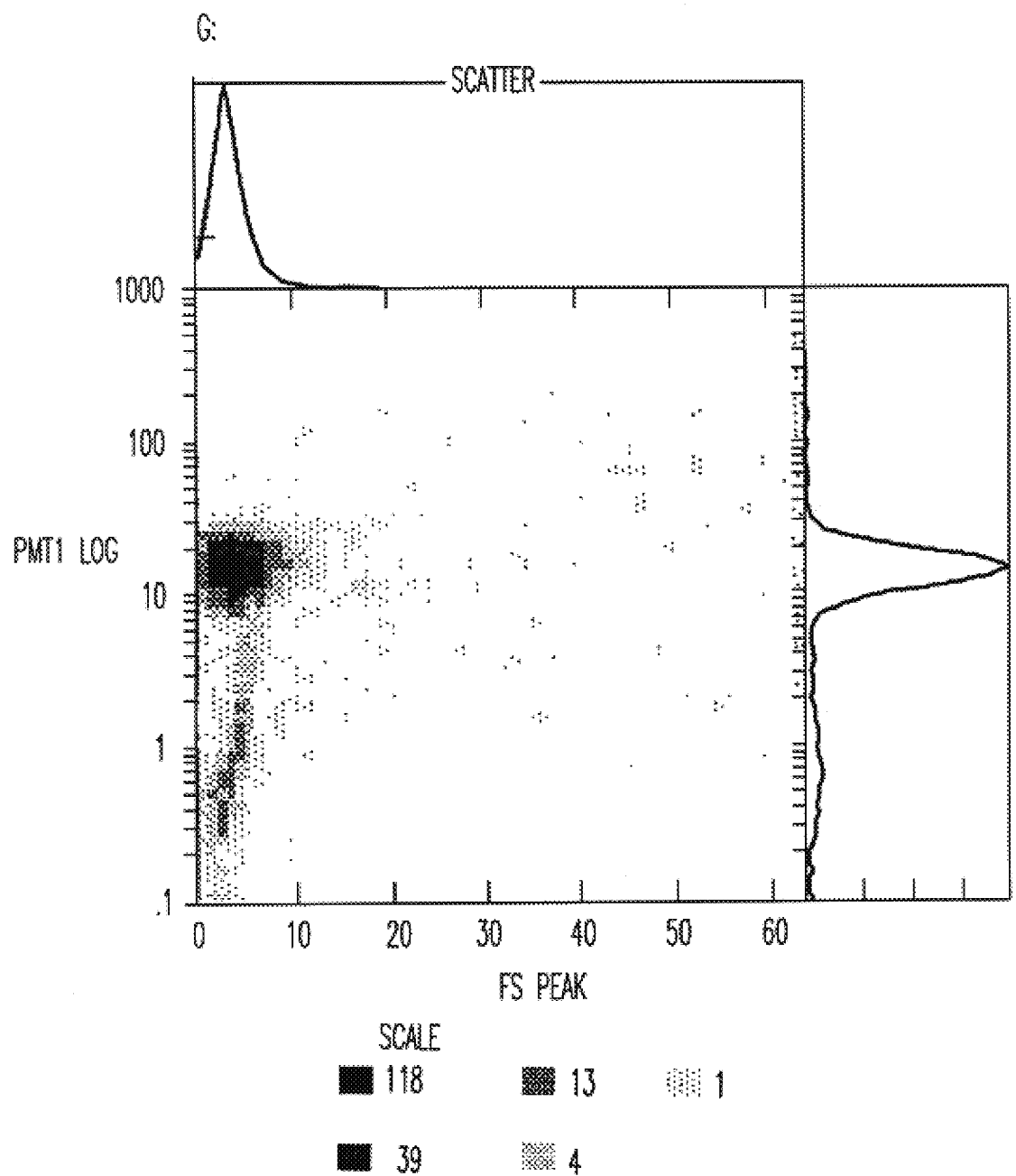
FIG. 1 shows a cell sorter cytogram (scattering light intensity distribution and integration) of agarose gel particulates encapsulating microbe cells, wherein the Y-axis represents the side scattering light intensity (SS) and the X-axis represents the forward scattering light intensity (FS) (Example 1).

The method of the present invention can be applied to any samples containing live microbe cells, including: those from mild environments such as soil, sludge, lake water, river water, marsh water, plants, and animals; those sampled from extreme environments, such as the deep sea, high-temperature or high-humidity regions, extremely cold regions, volcanic regions, high-acidity environments, dry environments; those sampled form natural environments where a mass of microbes of a small number of species exist due to, for example, rotting; those sampled from artificial environments such as the air in hospitals and active sludge from food factories, and materials for food processing industries (e.g., flavored soup); and those sampled from artificial special environments such as metal surfaces.

Any microbe species can be isolated by the method according to the present invention, irrespective of their classification. For example, true bacteria (e.g., bacteria and actinomycetes), archaebacteria (e.g., halophiles, high-temperature acidphiles, and methane-producing bacteria), eucaryotes (e.g., fungi, algae, and Protozoa), and viruses (including phages). In the conventional microbe isolation method (plate culture method), it is necessary to have prior knowledge of the nutritional and environmental conditions suitable for the growth of microbe species to be isolated. In contrast, the present invention enables, at least isolation of a single cell without knowing the nutritional and environmental conditions required for microbe species growth and isolation and this is advantageous over prior methods. The cell which would otherwise be difficult to isolate is isolated by encapsulating the sample of cells and selecting those that do not grow under the conditions of the cells capable of growing on a plate in the plate culture method.

When the sample is a solid, the solid is suspended in water that has been adjusted to have a pH, an osmotic pressure, a temperature and other similar factors to those of the sampling environment. When performing the suspension it is important to handle the microbes with care so as to prevent killing the microbes in the sample when, for example, the sample is taken from a special extreme environment. Particles and sediments larger than normal organisms are removed by an appropriate method as required, e.g., filtration, centrifugation and chromatography. If the number of live cells contained in the sample is presumed to be very high, preferably the sample solution is diluted to have live cells in an amount of about $1 \times 10^7$ cells/ml. Furthermore, because the number of live cells in a given sample is unknown it may be necessary to perform multiple dilutions of a single sample.

Microbe cells in the resultant sample solution are then encapsulated in agarose gel particulates. By this encapsulation, some of the agarose gel particulates encapsulate a single microbe cell, while others encapsulate more than one cell.

According to the present invention, it is preferable that the group of agarose gel particulates each of which encapsulates a single cell is large. The present inventors have found that a large group of agarose gel particulates each encapsulating a single cell can be obtained in the following manner.

First, the sample solution and an agarose solution are mixed at a temperature higher than a gelling temperature of the agarose. The concentration of the agarose in the solution can be 2% by weight although depending on the gelling temperature, the microbe species to be isolated and the like, the concentration can include from 0.1 to 20% by weight and all subranges and values therebetween. Preferably, an agarose with a low gelling temperature is used, such as Type VII (Low Gelling Temperature) distributed by Sigma. Furthermore, the gelling temperature should be suitably low as to be sufficient to maintain the viability of the microbe cells to be encapsulated.

Thereafter, the sample/agarose admixture is emulsified. Any method suitable for emulsifying the admixture can be used for the emulsification. For example, an inner pressure type membrane emulsification module (e.g., a model of SPG Techno) may be used. The emulsification by an inner pressure type emulsification module is as follows. A container is divided into two chambers with a membrane having appropriate micropores. One of the chambers has a means for pressurization, while the other chamber has a means for stirring. An oil (e.g., mineral oil such as Light White Oil distributed by Sigma) pre-adjusted to a temperature at which the agarose is not gelled is put into the stirring chamber, and the sample/agarose, which is pre-adjusted to a temperature where the agarose is not gelled, is put in the chamber for pressurization. When a pressure is applied to the chamber, the solution passes through the micropore of the membrane to the other unpressurized chamber wherein the sample/agarose that passes through the micropores is mixed with the oil thereby forming an emulsion.

The resultant emulsions are then cooled to a temperature below the gelling temperature of the agarose, to allow for formation of agarose gel particulates. If necessary, the resultant particulates are filtered with a 70-micron nylon mesh to remove large particles. By this process the number of agarose gel particulates which encapsulate a single cell can be increased.

When the agarose gel particulates encapsulating a single cell or plural of cells are placed in the nutritional and environmental conditions that enable the microbe that can grow on a plate of a conventional plate culture method to grow in the agarose gel particulate, the single cell capable of growing on a plate of a conventional plate culture method encapsulated in the agarose gel particulate will grow in the agarose gel particulate and multiply. The single cell which stays single in the agarose gel particulate after placing it in the nutritional and environmental conditions may be a cell of the microbe species that can not grow on a plate of a conventional plate culture method.

The nutritional and environmental conditions that enable the microbe that can grow on a plate of a plate culture method to grow in the agarose gel particulate is substantially the same as the nutritional and environmental conditions suitable for the plate culture of the microbes known to be contained in the sludge.

However, since it is preferred to culture (place in the nutritional and environmental conditions) the microbes encapsulated in agarose gel particulates by liquid culture (suspension of the agarose gel particulates in a liquid medium), the nutritional and environmental conditions designed for plate culture (solid culture) may be modified to correct the difference between the plate culture (solid culture) and the liquid culture. Such modification may include supplying liquid medium with gaseous oxygen. Other modifications are well known in the art.

Suitable nutritional end environmental conditions for microbes presumed to be contained in the sample can be determined by pre-testing. Alternatively, if the isolation source of sample is known, microbes expected to be contained in the sample can be presumed. Based on these presumptions, the nutritional and environmental conditions suitable for culture can be easily formulated accordingly.

When a variety of microbe species are expected to be contained in the sample, the agarose gel particulates may be incubated under several sets of conditions. This increases the probability of isolating a microbe species that otherwise could not be isolated from the sample.

The above nutritional and environmental conditions are therefore conditions desirable for the growth of a majority of microbes. In the case where a sample from an palaeobios or an extreme environment is to be isolated, it is necessary to consider the environment that is presumed to be desirable for such microbes expected to be contained in the sample. Otherwise, almost all microbes will be left included in the gel particulates as a single cell, or many microbes may even be killed. For example, when a sample from an acidic environment is to be examined, the acidic medium will be used for the isolation of microbes.

It should be noted that the above nutritional and environmental conditions are not necessarily conditions for growing all the microbe species, which would not likely be possible, but can be conditions that allow for distinguishing viable microbe species that can grow well from those that fail to grow.

Nutritional conditions include medium conditions, for example, media for samples from mild environments, in particular, include NUTRIENT BROTH and TRYPTIC SOY BROTH (DIFCO), GYP-S medium (solution of 1% glucose, 1% yeast extract, 0.5% peptone, 0.2% sodium acetate, 0.5% Tween80, and 0.5% salt solution, pH 6.8) for isolation of lactic acid bacteria, GYMP medium (solution of 1% glucose, 0.5% yeast extract, 0.3% malt extract, and 0.5% peptone, pH 6.0) suitable for growth of yeasts, acetic acid bacteria, lactic acid bacteria, and other suitable media conditions as disclosed, for example, in in Sambrook. Fritsch, and Maniatis, Molecular Cloning a Laboratory Manual, Cold Spring Harbor Laboratory Press, 1989, and Ausebel et al, Current Protocols in Molecular Biology, John Wiley and Sons, Inc., 1999. Environmental conditions include, for example, anaerobic/aerobic conditions, pH conditions, temperature conditions and osmotic conditions.

Preferably, the medium also contains an effective amount of a polysaccharide for promoting growth of the microbes. A preferred polysaccharide is selected from the group consisting of γ-cyclodextrin, 2-hydroxypropyl-β-cyclodextrin, 2,6-di-O-methyl-β-cyclodextrin, 2,3,6-tri-O-methyl-β-cyclodextrin, glycogen, pullulan, curdlan, cellulose and glucomannan.

It is possible to determine the number of cells encapsulated in the agarose gel particulate by observation with an optical microscope. However, the number of agarose gel particulates that can be observed with the optical microscope may be limited to a small number.

A cell sorter can be used to suitably distinguish an agarose gel particulate having a single cell from an agarose gel particulate having a number of cells. The cell sorter allows the analysis of a considerably large sample of agarose gel particulates. Moreover, the cell sorter provides for the identification and isolation of a single microbe cell even if the frequency of existence of such agarose gel particulates is low. Thus, the group of the agarose gel particulates having a single cell, which would not form a colony on the conventional plate culture, can be distinguished and isolated with high probability from the group of the agarose gel particulates having more than one cell.

A suitable cell sorter is, for example, the flow cytometry and cell sorting system, FC/CS, EPICS ELITE ESP (Courter) equipped with a 15 mW air-cooled argon ion laser. Likewise, any other system that has a similar function may also be used. In this cell sorter, a flow cell where the nozzle portion has a diameter of 100 μm, and the sample can be filtered using a cell strainer having a pore diameter of 40 μm prior to the start of the isolation operation of the sample to remove unnecessary coagulates. This pre-treatment may be performed as required.

The fractionation and distinguishing of the microbes (agarose gel particulates) are made by combining two (two-dimensional) or three (three-dimensional) out of three sorting parameters. These parameters include the forward scattering laser light intensity (FS) indicating the size of particles; the side scattering laser light intensity (SS) indicating the complexity of the inner structure of the particles; and the fluorescence intensity (FI) indicating whether or not cells are dyed with a specific fluorescent dye. In other words, an agarose gel particulate having a single cell can be distinguished from an agarose gel particulate having plural of cells using FS and SS. If required, whether the cell is alive or dead can be recognized using a fluorescent pigment (FL signal) with which live microbe can be dyed without being deadened. Examples of such pigments are carboxyfluorescein acetoxymethyl ester (CFDA) and carboxyfluorescein-diacetate acetoxymethyl ester (CFDA-AM).

The FS signal can be obtained by detecting 2° to 20° scattering light with a photodiode. The SS and FL signals can be obtained by converging light at 90° with respect to the laser light, splitting the converged light with a 488 nm dichroic long-pass filter, and detecting the split light with a photomultiplier tube. A scattering light fraction may be removed from self-fluorescent light using a 488 nm laser blocking filter.

The fluorescent light that is split with a 550 nm dichroic long-pass filter, and a light component that passes through a 525 nm pass filter can be determined as an FL1 signal (520–530 nm). A light component which passes through a 600 nm dichroic long-pass filter and a 575 band pass filter can be determined as an FL2 signal (570–580 nm), and a light component which passes through a 675 nm band pass filter can be determined as an FL3 signal (665–685 nm).

Thus, by isolating a single cell and examining the growth conditions for the isolated single cell whereby the single cell can actually grow, a microbe species that fails to be isolated under the known plate culture conditions can be isolated.

Having generally described this invention, a further understanding can be obtained by reference to certain specific examples which are provided herein for purposes of illustration only, and are not intended to be limiting unless otherwise specified.

EXAMPLES

Example 1

*Lactobacillus plantarum* NRIC1079 was used as sample bacteria. The sample bacteria were placed in a 5 ml GYP-S medium (pH 6 8) and left at 30° C. until the bacteria entered the late-stage logarithmic growth phase. The resultant liquid culture was diluted, with the aid of a microscope, in a phosphate buffered saline (PBS) solution to obtain a concentration of approximately $1 \times 10^7$ cells/ml. A 2% aqueous solution of agarose (Type VII of Sigma) was heated for 30 seconds in a microwave oven, dissolved, and maintained at 40° C.

The above microbe-containing dilute (1 ml) and the agarose solution (1 ml) were mixed and stirred with a vortex mixer at 40° C. The resultant mixture was extruded via a syringe into an SPG membrane (membrane emulsification module of SPG Techno) filled with mineral oil (Light White Oil distributed by Sigma) under pressure, and emulsified. The resultant emulsion was incubated under subfreezing conditions for five minutes to allow the agarose to gel. PBS was added to the resultant gel, and excessive mineral oil was washed off twice by centrifugation. The resultant gel was passed through a 70 μm strainer to obtain a filtered fraction.

The resultant agarose gel particulates were incubated in 5 ml of a GYP-S liquid medium (about $1 \times 10^6$ particles/5 ml) at 30° C. for 15 hours. Subsequently, 5 ml of pre-incubated agarose gel particulates were mixed with the incubated ones, and the resultant agarose gel particulates were charged into a cell sorter.

Figure 2:
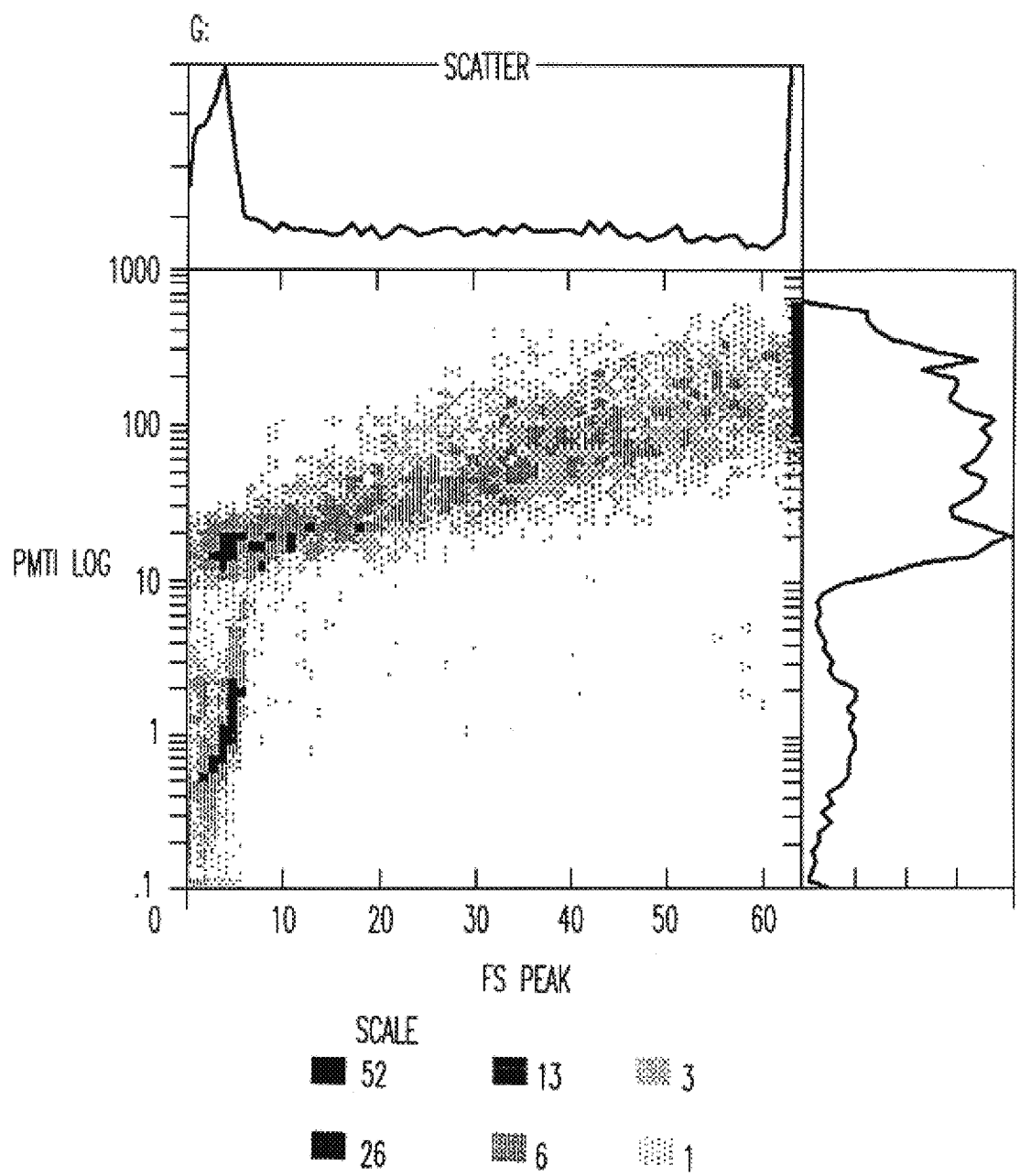
FIG. 2 shows a cell sorter cytogram (scattering light intensity distribution and integration) of agarose gel particulates including microbe cells, wherein the Y-axis represents the side scattering light intensity (SS) and the X-axis represents the front scattering light intensity (FS) (Example 1).

The EPICS ELITE ESP (Coulter) cell sorter equipped with a 15 mW air-cooled argon ion laser was used for the analysis. The flow cell had a nozzle portion with a diameter of 100 μm. The sample containing the agarose gel particulates was first filtered to remove coagulates using a cell strainer having a pore diameter of 40 μm. As the FS signal, 2° to 20° scattering light was detected with a photodiode. As the SS signal, light was converged at 90° with respect to the laser light, the converged light was split with a 488 nm dichroic long-pass filter, and the split light was detected with a photomultiplier tube. A scattering light fraction was removed from self-fluorescent light using a 488 nm laser blocking filter. One group of pre-incubated agarose gel particulates having a large SS signal was observed in a cell sorter cytogram (scattering light intensity distribution and integration) (FIG. 1). It was observed with a microscope that the agarose gel particulates in this group contained a single cell. In the case of the mixture of the pre-incubated agarose gel particulates and the post-incubated ones, observed in the cell sorter cytogram were two groups: a group located in the same area as the group of agarose gel particulates including a single cell described above; and a group of a band shape exhibiting FS and SS shifted to higher levels (FIG. 2). It was found by observation with the microscope that the agarose gel particulates in the band-shaped group included a plurality of cells. It was also found with CFDA dyeing that the cells in the agarose gel particulates including a single cell were alive.

active sludge aeration tank, and stirred sufficiently. The resultant solution was allowed to pass through a gauze and then a 35 μm strainer. The resultant filtrate was used as a microbe-containing sample solution.

The resultant sample solution was subjected to the process described in Example 1 to produce agarose gel particulates. The resultant agarose gel particulates were then mixed in 5 ml of NUTRIENT BROTH (DIFICO) (about $1\times10^6$ particles/5 ml) and stirred at 30° C. for 24 hours.

Incubated agarose gel particulates were sorted with a cell sorter as described in Example 1, and each of the agarose gel particulates having a single cell was isolated.

The each of the isolated cells (250 cells) was cultured in NUTRIENT BROTH (DIFICO) added with 10% (v/v) of the supernatant (6,000 rpm, 10 min.) of the activated sludge, and 10 cells grew in the modified NUTRIENT BROTH.

One (AS-8) of the 10 cells is classified to a novel species of the genus Paracoccus as mentioned below.

AS-8 had the taxonomic characteristics shown in Table 1.

TABLE 1

|  | AS-8 | P. denitrificans ATCC 17741 | P. aminovorans ATCC 49632 | P. aminophilus ATCC 49673 | P. Kocurii ATCC 49631 |
| --- | --- | --- | --- | --- | --- |
| Cell shape | short rod | short rod | short rod | short rod | short rod |
| Motility | − | − | − | − | − |
| Gram stain | − | − | − | − | − |
| Nitrate Reduction | + | + | + | + |  |
| PHB accumulation | + | + | + | + | + |
| Growth on NB |  |  |  |  |  |
| Sup. of As − | − | + | + | + | + |
| + | + | + | + | + | + |
| Growth in |  |  |  |  |  |
| 0% NaCl | + | + | + | + | + |
| 3% NaCl | − | + | + | + | − |
| 6% NaCl | − | − | − | − | − |
| 12% NaCl | − | − | − | − | − |
| Nitrogen source |  |  |  |  |  |
| KNO$_3$ | − | + | − | − | − |
| (NH$_4$)$_2$SO$_4$ | + | + | + | + | W |
| Glutamic acid | − | + |  |  | − |
| Utilization of |  |  |  |  |  |
| Xylose | − | − | − | + | − |
| Mannitol | − | + | + | − | − |
| Maltose | − | + | − | − | − |
| Lactose | − | − | − | + | − |
| Arabinose | + | − | − | − | − |
| Sucrose | + | − | − | − | − |
| Urease | + | + | − | − | − |
| Requirement | Unknown | No | VB1 | VB1 | VB1 |
| Major quinone | Q10 | Q10 | Q10 | Q10 | Q10 |
| G + C content (mol %) | 67 | 65–68 | 67 | 63 | 71 |
| Isolated from | AS | Soil | Soil | Soil | AS |

NB: NUTRIENT BROTH
NT: not tested
AS: activated sludge
PHB: poly(β-hydroxy-butyric acid)
W: week
Sup.: supernatant
VB1: thiamine Example 2

Ten milliliters of physical saline was added to 1 g of a sludge sample from a food manufacturer taken from an AS-8 is a short rod, gram-negative, nitrate-reducing and PHB-accumulating microbe, and thus belongs to the genus Paracoccus. AS-8 has the characteristics that it can not grow on a medium containing more than 0.3% NaCl, can not utilize potassium nitrate or glutamic acid but can utilize ammonium sulfate as the nitrogen source, has urease activity, and can not utilize xylose, mannitol or lactose but can utilize arabinose and sucrose as the carbon source. Other known species of the genus Paracoccus do not have these AS-8 characteristics.

DNA homology between AS-8 and the known species of the genus Paracoccus was determined by the DNA-DNA hybridization methods using the photo-biotin labeling- and microplate-method (T. Ezaki et al., Japanese Journal of Bacteriology 45, 851 (1990)). The results are shown in Table 2.

TABLE 2

|  | AS-8 | P. denitrificans ATCC 17741 | P. aminovorans ATCC 49632 | P. aminophilus ATCC 49673 | P. Kocurii ATCC 49631 |
|---|---|---|---|---|---|
| Homology (%) | 100 | 23 | 15 | 32 | 18 |

Figure 5:
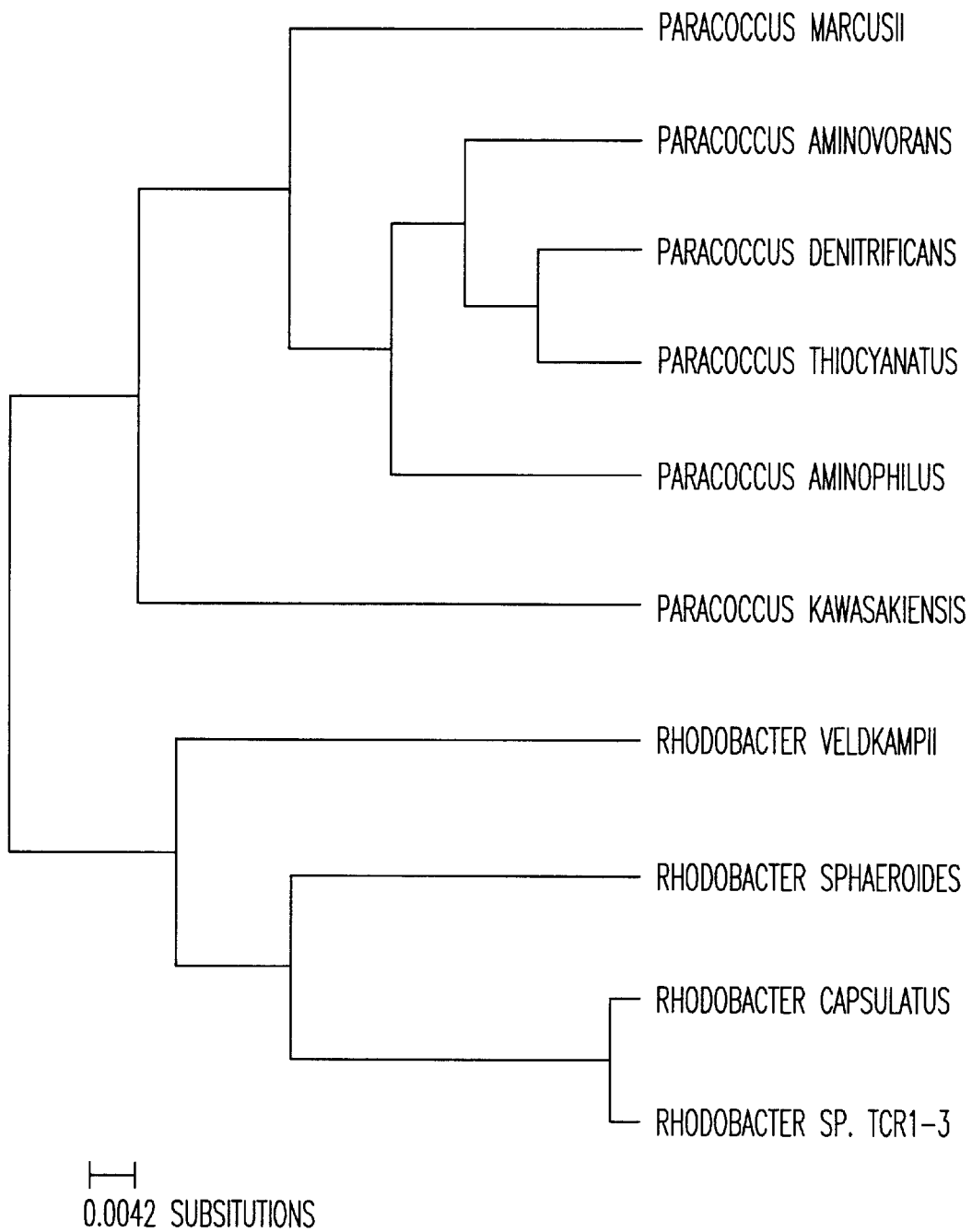
FIG. 5 shows a phylogenetic tree of Paracoccus-related microorganisms (Example 2).

The results in Table 2 show that the DNA homology of AS-8 with known species of Paracoccus is less than 70% and strongly suggests that AS-8 is distinct from the known species of the genus Paracoccus. Furthermore, the base sequence of a 16SrRNA (1.4 kb of N-terminus) of AS-8 was determined by conventional sequencing methods(SEQ ID NO: 1). The base sequence obtained was compared to other species registered at the GENBANK data base. The results of this comparison are represented by the phylogenetic tree shown in FIG. 5. The phylogenetic tree further demonstrates the relationship of AS-8 (*Paracoccus kawasakiensis*) as being distinct from the known species of Paracoccus and related microbial species.

The taxonomic study, DNA hybridization tests and homology analysis of 16SrRNA demonstrate that AS-8 is distinct from any of the known species of genus Paracoccus, and thus can be considered to be a novel species, and is designated as *Paracoccus kawasakiensis*.

*Paracoccus kawasakiensis* has been deposited under the Budapest Treaty on Nov. 16, 1999 with the accession number FERM-BP-7059 at Patent Microorganism Depository, National Institute of Bioscience and Human-Technology, Agency of Industrial Science (Japan).

Example 3

One gram of rotten melon was suspended in 10 ml of physical saline, and the resultant suspension was allowed to pass through a gauze and then a 35 μm strainer. The resultant filtrate was used as a sample solution.

The resultant sample solution was subjected to the process described in Example 1 to produce agarose gel particulates. The resultant agarose gel particulates were then mixed in 5 ml of a GYMP medium (about 1×10$^6$ particles/5 ml) and incubated at 30° C. for 3 hours.

The CFDA fluorescent pigment was added to the above mixture to obtain a concentration of 10 μ mols/ml, and was incubated for one hour. The incubated agarose gel particulates were sorted with a cell sorter as described in Example 1.

Figure 3:
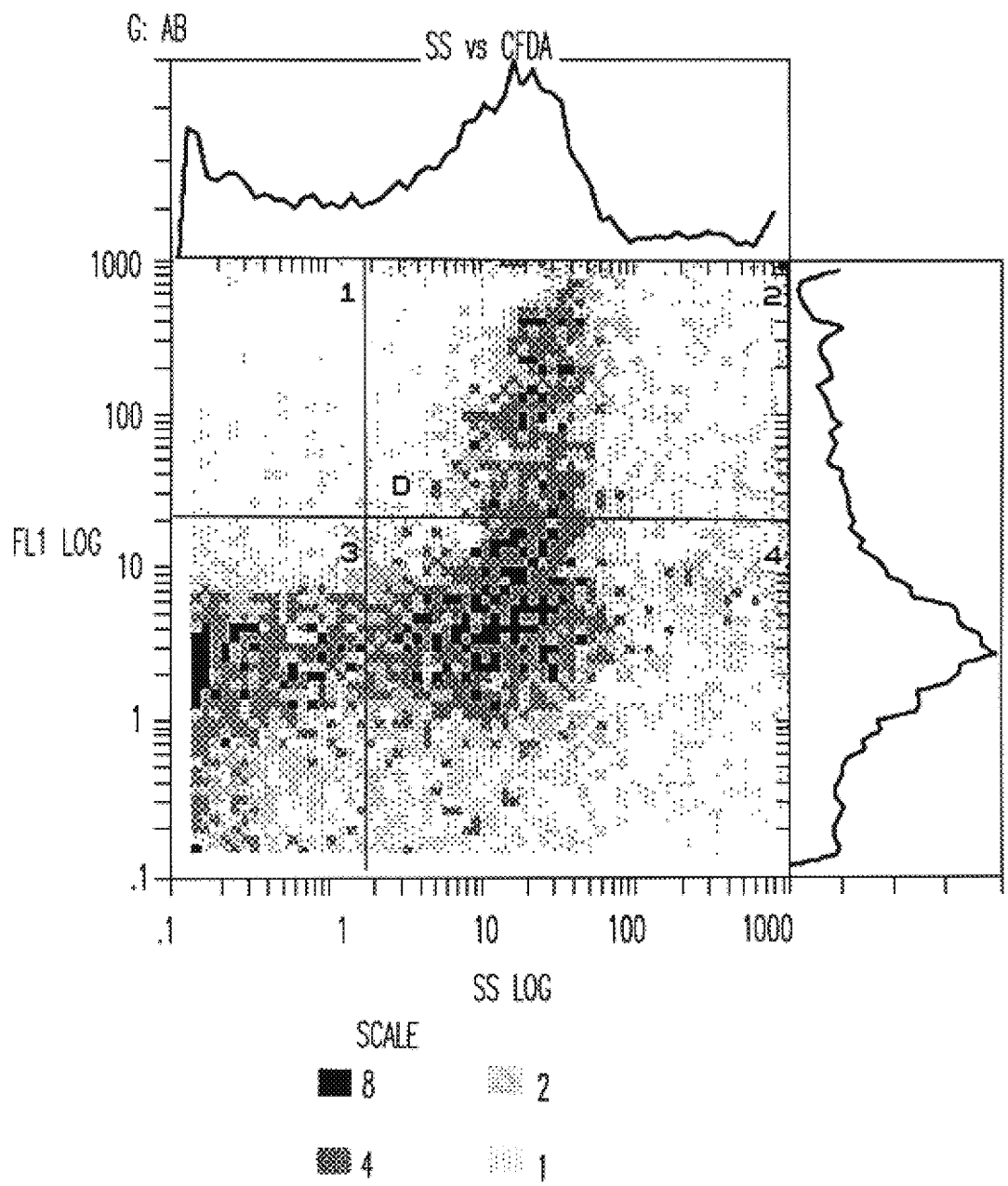
FIG. 3 shows a cell sorter cytogram (scattering light intensity distribution and integration) of agarose gel particulates including microbe cells, wherein the Y-axis represents the 520–530 nm fluorescence intensity (FL1) and the X-axis represents the side scattering light intensity (SS) (Example 3).
Figure 4:
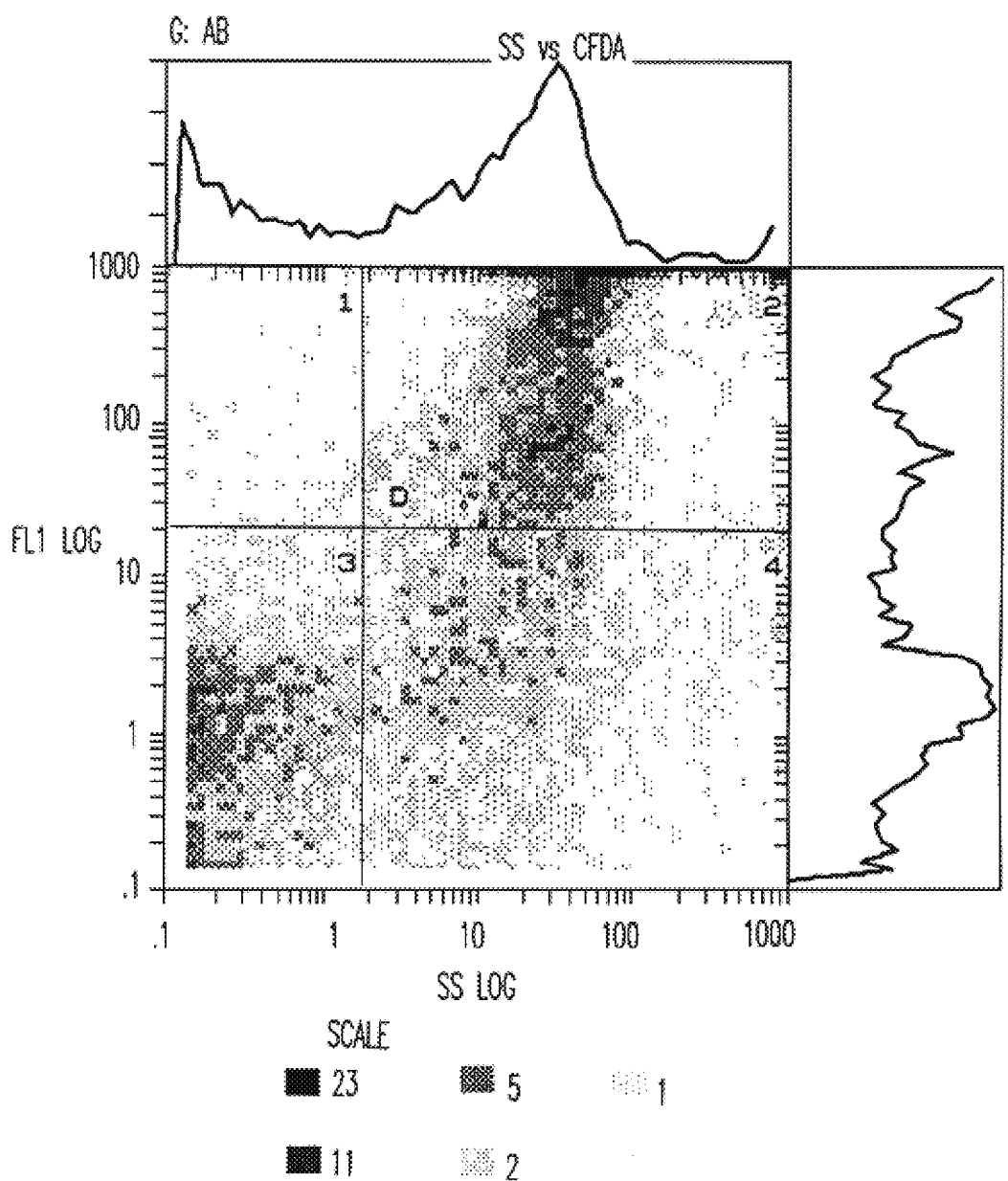
FIG. 4 shows a cell sorter cytogram (scattering light intensity distribution and integration) of agarose gel particulates including microbe cells, wherein the Y-axis represents the 520–530 nm fluorescence intensity (FL1) and the X-axis represents the side scattering light intensity (SS) (Example 3).

The results of the cell sorting analysis are as follows. Before the agarose gel particulates were placed in a growth environment, they were divided into roughly three groups (located lower left, upper light, and lower right of the cytogram as shown in FIG. 3). After they were placed in the growth conditions, the proportion of the group located in the lower right decreased, as observed in the cytogram shown in FIG. 4. The agarose gel particulates in the lower-right area were taken and observed with a microscope. It was found that each of the agarose gel particulates had a single cell and that the single cell was alive but failed to grow in the GYMP medium. Since the single cell could not grow in GYMP medium, the cell would not have been isolated by the conventional plate culture method. Thus, as described above, the method of the present invention makes it possible to isolate a single cell of a microbe species of which isolation would be difficult using the plate culture method.

Example 4

Ten ml of activated sludge obtained from a food manufacturer's factory were filtered through gauze. The filtered activated sludge was stirred, subjected to ultra-sonics, added with a saline solution, and further stirred to allow cells to disperse well in the filtered activated sludge. The cell dispersion was diluted with a saline solution to 3×10$^4$ cells/ml as determined by staining with 6-carboxy-fluorescein diacetate (J. Porter et al. J. Appl. Bacteriol., Vol. 79, 399–408 (1995)).

The medium used was NUTRIENT BROTH (DIFICO), an 1:3 mixture of Bact Beef® and Bact Peptone® added with 0.2% glucose and 2% agar. The medium was heat-sterilized and allowed to coagulate in plates. The plates were added with 0.1 w/w % of the compound shown in Table 3 and inoculated with 0.1 ml of the cell dispersion solution, and incubated at 30° C. After 2 or 10 days incubation, the number of colonies formed on the plates was counted.

As shown in Table 3, γ-cyclodextrin, 2-hydroxypropyl-β-cyclodextrin, 2,6-di-O-methyl-β-cyclodextrin and 2,3,6-tri-O-methyl-β-cyclodextrin promoted the growth of the microorganisms in the activated sludge.

TABLE 3

|  | Colony/plate formed after incubation of | |
|---|---|---|
| Cyclodextrin Compound | 2 days | 10 days |
| None | 125 | 320 |
| α-Cyclodextrin | 120 | 320 |
| β-Cyclodextrin | 105 | 350 |
| γ-Cyclodextrin | 210 | 640 |
| 2-Hydroxypropyl-β-cyclodextrin | 270 | 710 |
| 2,6-Di-O-methyl-β-cyclodextrin | 520 | 1,060 |
| 2,3,6-Tri-O-methyl-β-cyclodextrin | 220 | 650 |

Example 5

In the experiments of Example 4, the Cyclodextrin compound was replaced with 0.1 w/w % of the polysaccharide shown in Table 4. The polysaccharide shown in Table 4 promoted the growth of microorganisms in the activated sludge.

TABLE 4

|  | Colony/plate formed after incubation of | |
|---|---|---|
| Polysaccharide | 2 days | 10 days |
| None | 130 | 310 |
| Dextran | 146 | 350 |

TABLE 4-continued

| Polysaccharide | Colony/plate formed after incubation of | |
|---|---|---|
| | 2 days | 10 days |
| Glycogen | 210 | 830 |
| Pullulan | 180 | 600 |
| Curdlan | 220 | 745 |
| Cellulose | 244 | 685 |
| Glucomannan | 190 | 650 |

Example 6

Eight grams of NUTRIENT BROTH (DIFICO) and 2 g of glucose were mixed to obtain Medium (A). Medium (A) was further mixed with 1 g of glycogen (Medium(13)) or 1 g of 2,6-di-O-methyl-β-cyclodextrin (Medium (C)).

Fifty grams of soil were mixed with 10 mg of anthranilic acid and 10 g of the mixed soil were further mixed with 0.2 g of Medium (A), Medium (B) or Medium (C) to obtain Soil (A), Soil (B) or Soil (C).

Soil (A), Soil (B) and Soil (C) were placed in an incubator of 85% humidity at 30° C. for 10 days. Live cells in Soils (A) to (C) were counted on 5 and 10 days of incubation and anthranilic acid in Soil (A) to (C) were determined to determine the activity of microorganisms in the soil. The results are shown in Table 5.

TABLE 5

| | Cells/g-soil | | Anthranilic acid |
|---|---|---|---|
| | 5 days | 10 days | mg/g-soil |
| Soil (A) | $6 \times 10^7$ | $2 \times 10^8$ | 0.18 |
| Soil (B) | $5 \times 10^8$ | $1 \times 10^9$ | 0.12 |
| Soil (C) | $7 \times 10^8$ | $2 \times 10^9$ | 0.05 |

The results in Table 5 show that polysaccharides added to the nutrient media promote the growth of the microbes.

The priority documents JP 291297/99 filed Oct. 13, 1999, and JP 330419 filed Nov. 19, 1999 are hereby incorporated in their entirety by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A method for isolating a microbe comprising:
   encapsulating a sample of microbe cells in agarose gel particulates, wherein some of the particulates contain a single cell, and the other particulates contain more than one cell;
   incubating the particulates in nutritional and enviornmental conditions that enable the microbe contained in the sample that can grow on a plate of a plate culture method to grow in the agarose gel particulate; and
   isolating after said incubating the particulates having a single cell from the group of the agarose gel particulates having more than one cell.

2. The method according to claim 1, wherein the encapsulating comprises:
   mixing an agarose solution and the sample at a temperature higher than the gelling temperature of the agarose;
   adding an oil to the resultant mixture to form an emulsion; and
   gelling the agarose by lowering the temperature of the emulsion below the gelling temperature of the agarose.

3. The method of claim 2, wherein said agarose is a low melting temperature agarose.

4. The method of claim 2, wherein the concentration of said agarose in solution is 2% by weight.

5. The method according to claim 1, wherein said incubating is carried out in a medium comprising a polysaccharide selected from the group consisting of γ-cyclodextrin, 2-hydroxypropyl-β-cyclodextrin, 2,6-di-O-methyl-β-cyclodextrin, 2,3,6-tri-O-methyl-β-cyclodextrin, glycogen, pullulan, curdlan, cellulose and glucomannan.

6. The method of claim 1, wherein the isolating is carried out in a cell sorter.

7. The method of claim 6, wherein said isolating with a cell sorter comprises distinguishing the agarose gel particulates having a single cell from the agarose gel particulates having more than one cell using two sorting parameters, wherein the parameters are forward scattering laser light intensity and side scattering laser light intensity.

8. The method of claim 6, wherein said isolating with a cell sorter comprises distinguishing the agarose gel particulates having a single cell from the agarose gel particulates having more than one cell using three sorting parameters, wherein the parameters are forward scattering laser light intensity, side scattering laser light intensity, and fluorescent intensity.

9. The method of claim 1, wherein prior to said isolating the particulates are filtered.

10. The method of claim 1, wherein prior to said incubating the particulates are filtered.

11. The method of claim 1, wherein prior to said encapsulating the sample of microbe cells is filtered.

12. The method of claim 1, wherein said sample of microbe cells is diluted prior to encapsulating.

* * * * *

UNITED STATES PATENT AND TRADEMARK OFFICE
CERTIFICATE OF CORRECTION

PATENT NO.    : 6,391,576 B1
DATED         : May 21, 2002
INVENTOR(S)   : Tsuchida et al.

It is certified that error appears in the above-identified patent and that said Letters Patent is hereby corrected as shown below:

<u>Title page,</u>
Item [73], the Assignee information is incorrect. Item [73] should read as follows:
-- [73]   Assignees: Japan Bioindustry Association; Ajinomoto Co., Inc.; Secretary of Agency of Industrial Science and Technology, all of Tokyo (JP) --

Signed and Sealed this

Fifteenth Day of October, 2002

*Attest:*

*Attesting Officer*

JAMES E. ROGAN
*Director of the United States Patent and Trademark Office*